(12) United States Patent
Hoppe et al.

(10) Patent No.: US 6,589,520 B1
(45) Date of Patent: Jul. 8, 2003

(54) TREATMENT OF PSORIASIS, ALLERGIES AND AUTO-IMMUNE DISORDERS OF THE SKIN WITH CIS-6-HEXADECENOIC ACID

(75) Inventors: Udo Hoppe, Heidmühlen (DE); Jurgen Jacob, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/445,641

(22) PCT Filed: Apr. 3, 1998

(86) PCT No.: PCT/EP98/01949

§ 371 (c)(1),
(2), (4) Date: Apr. 17, 2000

(87) PCT Pub. No.: WO98/56371

PCT Pub. Date: Dec. 17, 1998

(30) Foreign Application Priority Data

Jun. 11, 1997 (DE) .......................................... 197 24 622

(51) Int. Cl.[7] .............................................. A61K 31/74
(52) U.S. Cl. ................ 424/78.05; 424/401; 424/78.02; 424/78.03; 514/887; 514/937
(58) Field of Search .............................. 424/401, 78.02, 424/78.03, 78.05, 78.06; 514/887, 937

(56) References Cited

U.S. PATENT DOCUMENTS 4,036,991 A * 7/1977 Stiefel ........................ 514/786
5,646,190 A 7/1997 Martin

FOREIGN PATENT DOCUMENTS

| DE | 41 31 940 | 1/1993 |
|----|-----------|--------|
| DE | 43 09 512 | 9/1994 |
| WO | 93/05752 | 4/1993 |
| WO | 94/21247 | 9/1994 |

* cited by examiner

Primary Examiner—Jose' G. Dees
Assistant Examiner—Konata M George
(74) Attorney, Agent, or Firm—Norris, McLaughlin & Marcus

(57) ABSTRACT

A method for the prophylaxes and treatment of psoriasis, allergies and auto-immune disorders of the skin, the treatment of sensitive skin, or a combination thereof, which comprises applying cis-6-hexadecenoic acid, or a salt or ester thereof.

2 Claims, No Drawings

TREATMENT OF PSORIASIS, ALLERGIES AND AUTO-IMMUNE DISORDERS OF THE SKIN WITH CIS-6-HEXADECENOIC ACID

The invention relates to novel compounds of cis-6-hexadec-1-enoic acid or its derivatives. It is also called cis-hexadec-6-enoic acid or delta-6-hexadecenoic acid.

BACKGROUND OF THE INVENTION

Saturated and unsaturated fatty acids are constituents of the cell membrane of cells. The concentration of unsaturated fatty acids plays a part in the barrier properties of the skin and in the reactivity of cells in inflammatory processes.

Thus it is already known to use cis-9-heptadecenoic acid for the treatment of psoriasis, allergies and auto-immune disorders (DE-A-4309512).

cis-6-Hexadecenoic acid has already been proposed for softening the skin in cosmetic and dermatological preparations (U.S. Pat. No. 4,036,991). It has also already been described in the literature that cis-hexadecenoic acid is a constituent of human sebaceous matter and psoriasis flakes (Jacob et al., Z. Klin. Chem. Klin. Biochem., 11th year, (1973), 297–300). A combination of neutral lipids with cis-6-hexadecenoic acid can be used for the treatment of dry skin (DE-A-4131940).

Surprisingly, it has been found that cis-6-hexadec-1-enoic acid is effective in psoriasis, allergies and auto-immune disorders as well as on dry skin and on sensitive skin.

SUMMARY OF THE INVENTION

The invention relates to the use of cis-6-hexadecenoic acid or its derivatives as an active compound for the prophylaxis and treatment of psoriasis, allergies and auto-immune disorders as well as on dry skin and on sensitive skin.

Topical application is preferred.

DETAILED DESCRIPTION

Highly suitable derivatives are the salts and esters of cis-6-hexadecenoic acid, which are preferred, and natural substances which contain this acid and its derivatives, which are also called derivatives here.

Preferred esters are the mono-, di- or trglycerides of cis-hexadecenoic acid, mixed glycerides which contain at least one further carboxylic acid or fatty acid, the mono- or di-cis-6-hexadecenoic acid esters with ethylene glycol and/or propylene glycol, where in each case one or more moles of glycol per mole or two moles of cis-hexadecenoic acid can be contained and cis-6-hexadecenoic acid esters with straight-chain or branched mono-alcohols having, for example, 1 to 22 carbon atoms, in particular 12 to 20 carbon atoms, in the alkyl radical.

Further carboxylic acids or fatty acids of the mixed triglycerides can contain, for example, 1 to 22, preferably 12 to 22, carbon atoms and can be saturated or unsaturated and then have, for example, 1 to 5, preferably 1 to 3, double bonds.

Suitable mono- or diesters with ethylene glycol and/or propylene glycol can contain, for example, 1 to 50, preferably 5 to 40, in particular 10 to 30, mol of glycol per mole of the respective ester.

cis-6-Hexadecenoic acid is the main constituent (85% by weight as the triglyceride) of the oil obtained from the seeds of Thunbergia alata, "black-eyed Susan" (G.F. Spencer et al., Lipids, Vol. 6, No. 10 and U.S. Pat. No. 4,036,991).

According to the invention, the natural triglycerides of the seed oil of Thunbergia alata with cis-6-hexadecenoic acid can preferably be used.

According to the invention, the seed oil of Thunbergia alata can also advantageously be used as a natural substance. It is thus, for example, not necessary to isolate the cis-6-hexadecenoic acid or its derivatives. It is also possible to use the active compounds according to the invention and in particular the seed oil of Thunbergia alata in pure form without further additives.

The oil can be obtained from the seeds in a simple manner, e.g. as described in the respected literature. The cis-6-hexadecenoic acid can then be obtained from the oil according to known processes, for example by ester cleavage, and from this in turn the derivatives according to the invention can be obtained by known processes.

The name psoriasis means this skin disorder of all types.

Allergies are, in particular, atopy and contact allergies. Atopy is manifested, for example, as allergic conjunctivitis, allergic rhinitis, allergic asthma or in particular neurodermatitis.

Auto-immune disorders are, in particular, the disorders of the rheumatic type.

Surprisingly, the active compounds according to the invention are effective against very different diseases such as psoriasis, allergies and auto-immune disorders, and on dry skin and on sensitive skin.

The active compounds according to the invention are distinguished by a strong anti-inflammatory action.

For prophylaxis, the active compounds are administered in order to decrease manifestations of the disease in frequency and strength. Treatment in the manifest stage leads to its curtailment and to the alleviation of the symptoms.

Even in the case of dry and sensitive skin, the active compounds can be used prophylatically and for the treatment of the disorders.

Dry skin is, on the one hand, skin which lacks an adequate or normal moisture content, but on the other hand also skin which suffers from structural damage and functional disorders in the epidermis and dermis, e.g. in addition to dryness with chapping and formation of dryness folds, pruritus and decreased refatting by sebaceous glands (for example after washing). The term "dry skin" also includes "senile xerosis".

The active compounds according to the invention can also be used in the case of sensitive skin, in particular against neurosensory phenomena, e.g. "stinging".

The epidermis is richly equipped with nerves and peripheroceptors such as Vater-Pacini lamellated corpuscles, Merkel cell neurite complexes and free nerve endings for sensation of pain, cold, heat and itching.

In humans with sensitive or easily injured skin, a neurosensory phenomenon called "stinging" ("sting=injure, bum, hurt) can therefore be observed. This "sensitive skin" differs basically from "dry skin" with thickened and indurated horny layers.

Typical reactions of "stinging" on sensitive skin are reddening, tautening and burning of the skin and also itching.

A further neurosensory phenomenon is to be regarded as itching in the case of atopic skin, and also itching in the case of skin disorders.

According to the invention, it is therefore possible to make available active compounds and preparations containing those active compounds which, in particular, prevent neurosensory phenomena or alleviate them or rapidly make them fade, i.e. are suitable for prophylaxis and/or treatment.

"Stinging" phenomena can be regarded as disorders to be treated cosmetically. Severe itching, however, in particular in the case of atopy, in particular neurodermatitis and severe itching of the skin occurring, can also be regarded as a relatively serious dermatological disorder.

The active compounds according to the invention can in particular also be used on skin superficially appearing to be healthy, e.g. in the case of psoriasis and atopy, i.e. also in addition to the diseased skin areas and, in particular, here too in the case of dry and sensitive skin.

Preferred salts are water-soluble salts of cis-9-heptadecenoic acid, in particular the alkali metal salts, e.g. the sodium salt or the potassium salt, and also the ammonium salt. Also suitable are the calcium, magnesium and aluminium salts and the salts of organic bases, e.g. amines such as ethanolamine, ethylenediamine and morpholine.

According to the invention, pharmaceutical preparations, agents or compositions are also provided which contain the compound according to the invention or its pharmaceutically tolerable salt together with a pharmaceutically tolerable diluent or vehicle.

The compounds of the present invention can be used orally or parenterally in man, e.g. in a dosage of 0.05 to 500 mg, preferably 0.5 to 50 mg, particularly preferably 0.1 to 10 mg per day, in particular also in subdivided doses, for example twice to four times daily.

The active compounds according to the invention can also be incorporated without problems into customary pharmaceutical, in particular dermatological, and cosmetic bases for preferred topical applications and the corresponding pharmaceutical, in particular dermatological, and cosmetic topical preparations or compositions can thus be obtained. Preferably, they are employed in amounts from 0.001 to 10% by weight, in particular in amounts from 0.01 to 1% by weight, in each case based on the total weight of the topical composition. Amounts of over 0.5% by weight, e.g. 0.51% by weight to 10% by weight are also preferred, and also amounts in the range from 0.001 to 0.05 or 0.049% by weight. The preparations can be used daily in a customary manner.

The invention also relates to the use of the active compounds according to the invention for the production of pharmaceutical compositions, in particular topical pharmaceutical and cosmetic compositions for the prophylaxis and treatment of psoriasis, allergies and auto-immune disorders and on dry skin and on sensitive skin.

Likewise, the invention also relates to the use of pharmaceutical compositions and topical pharmaceutical and cosmetic preparations containing cis-6-hexadecenoic acid or its derivatives for the prophylaxis and treatment of psoriasis, allergies and auto-immune disorders and on dry skin and on sensitive skin.

In the macrophage differentiation test, cis-6-hexadecenoic acid showed an anti-inflammatory macrophage-stimulating potency. This is of importance in the prophylaxis of processes such as, for example, psoriasis or atopy or allergies or auto-immune disorders.

The invention also relates to the use of the active compounds according to the invention as antibacterial active compounds, e.g. in the preparations mentioned, in particular in topical preparations, e.g. in the amounts mentioned.

They are preferably used against gram-positive bacteria, in particular against Micrococcus luteus.

The active compounds according to the invention can be mixed with customary pharmaceutically tolerable diluents or vehicles and, if appropriate, with other auxiliaries and administered, for example, orally or parenterally. They can preferably be administered orally in the form of granules, capsules, pills, tablets, film-coated tablets, sugar-coated tablets, syrups, emulsions, suspensions, dispersions, aerosols and solutions and also liquids, or else also as suppositories, vaginal suppositories or parenterally, e.g. in the form of solutions, emulsions or suspensions. Preparations to be administered orally can contain one or more additives such as sweeteners, aromatizing agents, colourants and preservatives. Tablets can contain the active compound mixed with customary pharmaceutically tolerable auxiliaries, for example inert diluents such as calcium carbonate, sodium carbonate, lactose and talc, granulating agents and agents which promote the disintegration of the tablets on oral administration, such as starch or alginic acid, binding agents such as starch or gelatin, lubricants such as magnesium stearate, stearic acid and talc.

Suitable excipients are, for example, lactose, gelatin, maize starch, stearic acid, ethanol, propylene glycol, ethers of tetrahydrofurfuryl alcohol and water.

The formulations are prepared, for example, by extending the active compounds with solvents and/or excipients, if appropriate using emulsifiers and/or dispersants, it being possible, for example, in the case of the use of water as a diluent optionally to use organic solvents as auxiliary solvents.

Administration is carried out in a customary manner, preferably orally or parenterally, in particular perlingually or intravenously. In the case of oral administration, apart from the excipients mentioned, tablets, of course, can also contain additives, such as sodium citrate, calcium carbonate and dicalcium phosphate together with various additives, such as starch, preferably potato starch, gelatin and the like. Furthermore, lubricants such as magnesium stearate, sodium lauryl sulphate and talc can additionally be used for tableting. In the case of aqueous suspensions and/or elixirs, which are intended for oral administration, the active compounds can be mixed, apart from with the abovementioned auxiliaries, with various flavour enhancers or colourants.

In the case of parenteral administration, solutions of the active compounds using suitable liquid excipients can be employed.

Capsules can contain the active compound as a single constituent or mixed with a solid diluent such as calcium carbonate, calcium phosphate or kaolin. The injectable preparations are also formulated in a manner known per se.

The pharmaceutical preparations can contain the active compound in an amount from 0.1 to 90% by weight, in particular 1–90% by weight. Capsules are particularly preferred. Individual doses contain the active compounds preferably in an amount from 1 to 10 mg.

If salts are sparingly soluble in water, they can be administered in the form of suspensions. The sodium and the potassium salts of cis-9-heptadecenoic acid have a particularly good solubility in water. For example, salts are preferably injected intravenously or intramuscularly in the form of an aqueous solution, such as physiological saline solution. The ampoules contain, for example, 2.5 mg of the fatty acid salt per 5 ml of solution. Ampoules containing, for example, 45 mg of fatty acid salt per milliliter of solution can also be prepared.

The particularly preferred topical compositions according to the invention can be formulated as liquid, pasty or solid preparations, for example as aqueous or alcoholic solutions, aqueous suspensions, emulsions, for example W/O or O/W emulsions, ointments, gels, lotions, creams, oils, powders or sticks. Depending on the desired formulation, the active compounds can be incorporated into pharmaceutical and cosmetic bases for topical application, which as further components contain, for example, oil components, fat and waxes, emulsifiers, anionic, cationic, ampholytic, zwitterionic and/or non-ionic surfactants, lower mono- and polyhydric alcohols, water, preservatives, buffer substances, thickeners, fragrances, colourants and opacifiers. Preferably, the emulsions, e.g. W/O emulsions, or ointments are used.

Furthermore, it is preferred according to the invention to add antioxidants to the active compounds and to the pharmaceutical and topical preparations. The use of natural or naturally identical compounds such as, for example, tocopherols is particularly preferred here. The antioxidants mentioned are contained in the compositions according to the invention, for example, in amounts from 0.01–5% by weight, in particular from 0.5–2% by weight, based on the total composition.

In the context of the present application, if not stated otherwise, amounts and percentage data are based on the weight and the total composition or preparation.

Example 1

| Cream: | Parts by weight |
| --- | --- |
| Polyoxyethylene(20) sorbitan monostearate (polysorbate 60) | 5 |
| Cetylstearyl alcohol | 10 |
| Glycerol 85% | 10 |
| White petroleum jelly | 25 |
| α-D-Tocopherol | 1 |
| cis-6-Hexadecenoic acid Na salt | 1 |
| If appropriate colourants, fragrances | |
| Water | to 100 |

The preparation is carried out in a manner known per se. The fat phase and the aqueous phase are prepared separately by mixing the constituents, if appropriate with slight warming. The phases are then mixed and emulsified.

Example 2

| Cream: | Parts by weight |
| --- | --- |
| Polyoxyethylene(20) sorbitan monostearate (polysorbate 60) | 5 |
| Cetylstearyl alcohol | 10 |
| Glycerol 85% | 10 |
| White petroleum jelly | 25 |
| α-D-Tocopherol | 1 |
| cis-6-Hexadecenoic acid | 0.1 |
| If appropriate colourants, fragrances | |
| Water | to 100 |

The preparation is carried out in a manner known per se. The fat phase and the aqueous phase are prepared separately by mixing the constituents, if appropriate with slight warming. The phases are then mixed and emulsified.

Preparation of Tablets and Capsules

Tablets and capsules which contain the constituents indicated below are prepared according to known working procedures. These are suitable for the treatment of the abovementioned diseases in dosage amounts of one tablet or capsule in each case once or a number of times daily.

Example 3

| | Weight (mg) | |
| --- | --- | --- |
| Constituents | Tablet | Capsule |
| cis-6-Hexadecenoic acid | 5 | 10 |
| Tragacanth | 10 | |
| Lactose | 247.5 | |
| Maize starch | 25 | |
| Talc | 15 | |
| Magnesium stearate | 2.5 | |
| Ascorbic acid | 1 | 0.1 |

Example 4

| | Weight (mg) | |
| --- | --- | --- |
| Constituents | Tablet | Capsule |
| cis-6-Hexadecenoic acid Na salt | 10 | 5 |
| Tragacanth | 10 | |
| Lactose | 247.5 | |
| Maize starch | 25 | |
| Talc | 15 | |
| Magnesium stearate | 2.5 | |
| Ascorbic acid | 1 | 0.1 |

Preparation of Ampoules

Ampoules which contain the constituents mentioned below can be prepared in a known manner. The active compound is dissolved in water and dispensed into glass ampoules under nitrogen.

Example 5

| cis-6-Hexadecenoic acid Na salt | 5 mg |
| --- | --- |
| Dist. water to | 5 ml |

Example 6

| cis-6-Hexadecenoic acid Na salt | 2.5 mg |
| --- | --- |
| Dist. water to | 2 ml |

Example 7

| Polyoxyethylene(20) sorbitan monostearate (polysorbate 60) | 5 |
| --- | --- |
| Cetyl/stearyl alcohol (cetostearyl alcohol) | 10 |
| Glycerol 85% | 10 |
| White petroleum jelly | 25 |
| α-D-Tocopherol | 1 |
| cis-6-Hexadecenoic acid triglyceride | 1 |
| If appropriate colourants, fragrances | |
| Water | to 100 |

The preparation is carried out in a manner known per se. The fatty phase and the aqueous phase are prepared separately by mixing the constituents, if appropriate with slight warming. The phases are then mixed and emulsified.

Example 8

| Cream: | Parts by weight |
| --- | --- |
| Polyoxyethylene(20) sorbitan monostearate (polysorbate 60) | 5 |
| Cetyl/stearyl alcohol (cetostearyl alcohol) | 10 |
| Glycerol 85% | 10 |
| White petroleum jelly | 25 |
| α-D-Tocopherol | 1 |
| cis-6-Hexadecenoic acid triglyceride | 0.1 |
| If appropriate colourants, fragrances | |
| Water | to 100 |

The preparation is carried out in a manner known per se. The fatty phase and the aqueous phase are prepared separately by mixing the constituents, if appropriate with slight warming. The phases are then mixed and emulsified.

Example 9

| Cream: | Parts by weight |
| --- | --- |
| Polyoxyethylene(20) sorbitan monostearate (polysorbate 60) | 5 |
| Cetyl/stearyl alcohol (cetostearyl alcohol) | 10 |
| Glycerol 85% | 10 |
| White petroleum jelly | 25 |
| α-D-Tocopherol | 1 |
| Seed oil of *Thunbergia alata* | 1 |
| If appropriate colourants, fragrances | |
| Water | to 100 |

Example 10

| Cream: | Parts by weight |
| --- | --- |
| Polyoxyethylene(20) sorbitan monostearate (polysorbate 60) | 5 |
| Cetyl/stearyl alcohol (cetostearyl alcohol) | 10 |
| Glycerol 85% | 10 |
| White petroleum jelly | 25 |
| α-D-Tocopherol | 1 |
| Seed oil of *Thunbergia alata* | 0.1 |
| If appropriate colourants, fragrances | |
| Water | to 100 |

The preparation is carried out in a manner known per se. The fatty phase and the aqueous phase are prepared separately by mixing the constituents, if appropriate with slight warming. The phases are then mixed and emulsified.

What is claimed is:

1. A method for the prophylaxis and treatment of psoriasis, allergies and auto-immune disorders of the skin, the treatment of sensitive skin, or a combination thereof, which comprises applying to said skin a composition in which the active ingredient for the prophylaxis or treatment consists essentially of cis-6-hexadecenoic acid, or a salt or ester thereof.

2. A method for the prophylaxis and treatment of psoriasis, allergies and auto-immune disorders of the skin, the treatment of sensitive skin, or a combination thereof, which comprises administering orally or parenterally a composition in which the active ingredient for the prophylaxis or treatment comprises cis-6-hexadecenoic acid, or a salt or ester thereof.

* * * * *